US011918780B2

(12) United States Patent
Jagelski et al.

(10) Patent No.: US 11,918,780 B2
(45) Date of Patent: Mar. 5, 2024

(54) AGENT ADMINISTERING MEDICAL DEVICE

(71) Applicant: Boston Scientific Scimed, Inc., Maple Grove, MN (US)

(72) Inventors: Matthew Robert Jagelski, Marlborough, MA (US); Andrew Pic, Northboro, MA (US); Amanda Lynn Smith, Boston, MA (US); Ra Nam, Lawrence, MA (US); Laurie A. Lehtinen, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 535 days.

(21) Appl. No.: 17/108,495

(22) Filed: Dec. 1, 2020

(65) Prior Publication Data

US 2021/0162121 A1 Jun. 3, 2021

Related U.S. Application Data

(60) Provisional application No. 62/942,988, filed on Dec. 3, 2019.

(51) Int. Cl.
*A61M 5/155* (2006.01)
*A61M 5/145* (2006.01)
*A61M 5/315* (2006.01)

(52) U.S. Cl.
CPC .......... *A61M 5/155* (2013.01); *A61M 5/1454* (2013.01); *A61M 5/31586* (2013.01);
(Continued)

(58) Field of Classification Search
CPC .......... A61M 15/0036; A61M 15/0038; A61M 15/004; A61M 15/0085; A61M 15/0021;
(Continued)

(56) References Cited

U.S. PATENT DOCUMENTS 471,854 A 3/1892 Howard
881,238 A 3/1908 Hasbrouck
(Continued)

FOREIGN PATENT DOCUMENTS

CN 101401956 B 11/2012
CN 110064110 A 7/2019
(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Jason E Flick
*Assistant Examiner* — Justin L Zamory
(74) *Attorney, Agent, or Firm* — Bookoff McAndrews, PLLC

(57) ABSTRACT

A medical device comprising an enclosure defining a cavity for containing agent, a lumen for receiving a pressurized gas, and a barrier positioned between the cavity and the lumen, the barrier including at least one opening for storing agent, wherein rotation of the barrier relative to the lumen establishes fluid communication between the at least one opening and the lumen for delivering agent from the at least one opening to the lumen.

20 Claims, 6 Drawing Sheets

(52) U.S. Cl.
CPC ............... *A61M 2202/0225* (2013.01); *A61M 2210/0625* (2013.01); *A61M 2210/105* (2013.01); *A61M 2210/1053* (2013.01); *A61M 2210/1067* (2013.01)

(58) Field of Classification Search
CPC ............ A61M 15/0041; A61M 15/005; A61M 15/0045; A61M 15/0048; A61M 11/005; A61M 11/007; A61M 2202/0225; A61M 2210/0625; A61M 2210/105; A61M 2210/1053; A61M 2210/1067
See application file for complete search history.

(56) References Cited

U.S. PATENT DOCUMENTS 1,145,520 A 7/1915 Smith
1,599,959 A 9/1926 Buheiji
1,732,566 A 10/1929 McKendrick
2,151,418 A 3/1939 Bolté
2,185,927 A 6/1940 Shelanski
2,478,715 A 8/1949 Schmitt
2,623,519 A 12/1952 Cohen
3,669,113 A 6/1972 Altounyan et al.
3,940,061 A 2/1976 Gimple et al.
4,184,258 A 6/1980 Barrington et al.
4,427,450 A 1/1984 Kostansek
4,457,329 A 7/1984 Werley et al.
4,534,345 A 8/1985 Wetterlin
4,806,167 A 2/1989 Raythatha
5,215,221 A 6/1993 Dirksing
5,231,983 A 8/1993 Matson et al.
5,273,531 A 12/1993 Knoepfler
5,312,331 A 5/1994 Kneopfler
5,312,333 A 5/1994 Churinetz et al.
5,366,122 A 11/1994 Guentert et al.
5,388,572 A * 2/1995 Mulhauser ............ B05B 11/061 128/204.13
5,445,612 A 8/1995 Terakura et al.
5,470,311 A 11/1995 Setterstrom et al.
5,884,621 A 3/1999 Matsugi et al.
5,951,531 A 9/1999 Ferdman et al.
6,003,512 A 12/1999 Gerde
6,484,750 B1 11/2002 Foos et al.
6,554,022 B2 4/2003 Wakeman
6,589,087 B2 7/2003 Mackal et al.
6,684,917 B2 2/2004 Zhu et al.
6,708,712 B2 3/2004 Wakeman
6,716,190 B1 4/2004 Glines et al.
6,799,571 B1 10/2004 Hughes et al.
7,178,547 B2 2/2007 Mackal
7,311,270 B2 12/2007 Kapila
7,334,598 B1 2/2008 Hollars
7,361,300 B2 4/2008 Kelly et al.
7,427,607 B2 9/2008 Suzuki
7,455,248 B2 11/2008 Kablik et al.
7,461,649 B2 12/2008 Gamard et al.
7,544,177 B2 6/2009 Gertner
7,563,299 B2 7/2009 Baptista da Costa et al.
7,673,647 B2 3/2010 Mackal
7,841,338 B2 11/2010 Dunne et al.
7,892,205 B2 2/2011 Palasis et al.
7,921,874 B2 4/2011 Tekulve et al.
8,037,880 B2 10/2011 Zhu et al.
8,097,071 B2 1/2012 Burgess et al.
8,118,777 B2 2/2012 Ducharme et al.
8,269,058 B2 9/2012 McCarthy et al.
8,313,474 B2 11/2012 Campbell et al.
8,360,276 B2 1/2013 Rogier et al.
8,361,054 B2 1/2013 Ducharme et al.
8,496,189 B2 7/2013 Lomond et al.
8,673,065 B2 3/2014 Burgess et al.
8,721,582 B2 5/2014 Ji
8,728,032 B2 5/2014 Ducharme et al.
8,741,335 B2 6/2014 McCarthy
8,827,980 B2 9/2014 Ji
8,910,627 B2 12/2014 Iwatschenko et al.
8,951,565 B2 2/2015 McCarthy
9,028,437 B2 5/2015 Ott et al.
9,089,658 B2 7/2015 Dunne et al.
9,101,744 B2 8/2015 Ducharme
9,107,668 B2 8/2015 Melsheimer et al.
9,132,206 B2 9/2015 McCarthy
9,204,957 B2 12/2015 Gregory et al.
9,205,170 B2 12/2015 Lucchesi et al.
9,205,207 B2 12/2015 Ji
9,205,240 B2 12/2015 Greenhalgh et al.
9,308,584 B2 4/2016 Burgess et al.
9,310,812 B2 4/2016 Costle et al.
9,375,533 B2 6/2016 Ducharme et al.
9,492,646 B2 11/2016 Hoogenakker et al.
9,517,976 B2 12/2016 Mackal
9,545,490 B2 1/2017 Iwatschenko et al.
9,555,185 B2 1/2017 Foster et al.
9,629,966 B2 4/2017 Ji
9,636,470 B2 5/2017 Pohlmann et al.
9,707,359 B2 7/2017 Kubo
9,713,682 B2 7/2017 Eistetter et al.
9,717,897 B2 8/2017 Rogier
9,821,084 B2 11/2017 Diegelmann et al.
9,839,772 B2 12/2017 Ducharme
9,839,774 B2 12/2017 Bonaldo
9,846,439 B2 12/2017 Carman et al.
9,867,931 B2 1/2018 Gittard
9,976,660 B2 5/2018 Stanton et al.
10,004,690 B2 6/2018 Lee et al.
10,010,705 B2 7/2018 Greenhalgh et al.
10,017,231 B2 7/2018 Fawcett, Jr.
10,036,617 B2 7/2018 Mackal
10,065,004 B2 9/2018 Eder et al.
10,173,019 B2 1/2019 Kaufmann et al.
10,384,049 B2 8/2019 Stanton et al.
10,463,811 B2 11/2019 Lee et al.
10,507,293 B2 12/2019 Goodman et al.
10,646,706 B2 5/2020 Rogier
10,730,595 B2 8/2020 Fawcett
10,751,523 B2 8/2020 Rogier
10,806,853 B2 10/2020 Gittard
10,840,814 B2 12/2020 Fawcett
10,850,814 B2 12/2020 Fawcett
10,994,818 B2 5/2021 Hernandez
2004/0107963 A1 6/2004 Finlay et al.
2004/0249359 A1 12/2004 Palasis et al.
2005/0121025 A1 6/2005 Gamard et al.
2005/0147656 A1 7/2005 McCarthy et al.
2005/0220721 A1 10/2005 Kablik et al.
2006/0004314 A1 1/2006 McCarthy et al.
2006/0213514 A1 9/2006 Price et al.
2007/0056586 A1 3/2007 Price et al.
2007/0066920 A1 3/2007 Hopman et al.
2007/0066924 A1 3/2007 Hopman et al.
2007/0082023 A1 4/2007 Hopman et al.
2007/0125375 A1 6/2007 Finlay et al.
2007/0151560 A1 7/2007 Price et al.
2007/0083137 A1 8/2007 Hopman et al.
2007/0199824 A1 8/2007 Hoerr et al.
2008/0021374 A1 1/2008 Kawata
2008/0287907 A1 11/2008 Gregory et al.
2009/0101144 A1 4/2009 Gamard et al.
2009/0155342 A1 6/2009 Diegemann et al.
2009/0281486 A1 11/2009 Ducharme
2010/0121261 A1 5/2010 Kablik et al.
2010/0305505 A1 12/2010 Ducharme et al.
2011/0073200 A1 3/2011 Overvaag et al.
2011/0274726 A1 11/2011 Guo et al.
2011/0308516 A1 12/2011 Price et al.
2012/0304991 A1* 12/2012 Gotliboym ........ A61M 15/0025 128/203.15
2014/0271491 A1 9/2014 Gittard et al.
2015/0094649 A1 4/2015 Gittard
2015/0125513 A1 5/2015 McCarthy
2016/0375202 A1 12/2016 Goodman et al.
2017/0106181 A1 4/2017 Bonaldo et al.
2017/0232141 A1 8/2017 Surti et al.

(56) References Cited

U.S. PATENT DOCUMENTS

| | | | |
|---|---|---|---|
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |
| 2019/0232030 A1* | 8/2019 | Pic | A61M 11/02 |
| 2021/0024187 A1 | 1/2021 | Fawcett et al. | |
| 2021/0069485 A1 | 3/2021 | Rogier | |

FOREIGN PATENT DOCUMENTS

| | | | |
|---|---|---|---|
| DE | 60215438 | T2 | 8/2007 |
| EP | 3052168 | B1 | 11/2019 |
| JP | H07118305 | A | 5/1995 |
| WO | 03013552 | A1 | 2/2003 |
| WO | 2004066806 | A2 | 8/2004 |
| WO | 2005062896 | A2 | 7/2005 |
| WO | 2006071649 | A2 | 7/2006 |
| WO | 2006088912 | A2 | 8/2006 |
| WO | 2008033462 | A2 | 3/2008 |
| WO | 2009061409 | A1 | 5/2009 |
| WO | 2011059968 | A1 | 5/2011 |
| WO | 2015050814 | A1 | 4/2015 |
| WO | 2018157772 | A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, COOK, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion dated Feb. 19, 2021 in counterpart International Patent Application No. PCT/US2020/062696 (12 pages, in English).

* cited by examiner

AGENT ADMINISTERING MEDICAL DEVICE

CROSS-REFERENCE TO RELATED APPLICATIONS

This application claims the benefit of priority from U.S. Provisional Application No. 62/942,988, filed on Dec. 3, 2019, which is incorporated by reference herein in its entirety.

TECHNICAL FIELD

The present disclosure relates generally to a medical device that administers an agent. More particularly, at least some embodiments of the present disclosure relate to a medical device including a system that can be actuated to administer a dosage of an agent to a lumen.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY OF THE DISCLOSURE

According to an example, a medical device may comprise an enclosure defining a cavity for containing agent, a lumen for receiving a pressurized gas, and a barrier positioned between the cavity and the lumen, the barrier including at least one opening for storing agent, wherein rotation of the barrier relative to the lumen establishes fluid communication between the at least one opening and the lumen for delivering agent from the at least one opening to the lumen. A bottom end of the cavity may include a wall adjacent to the barrier, wherein the wall includes a wall opening, wherein the wall opening is located on an area of the wall so that the wall opening is aligned with the at least one opening via rotation of the barrier. Alignment of the wall opening with the at least one opening may permit agent from the enclosure to enter the at least one opening. The enclosure may be rotatable relative to the barrier and/or the lumen. The barrier may be rotatable relative to the enclosure. The agent may remain in the at least one opening until fluid communication between the at least one opening and the lumen is established. The enclosure may feed the at least one opening with agent via gravity. The at least one opening for storing agent may feed the lumen with agent via gravity when fluid communication between the at least one opening and the lumen is established.

In another example, the at least one opening for storing agent may be a plurality of openings arranged radially about the barrier. The plurality of openings may be symmetrically arranged. Each of the plurality of openings may be different in size. When fluid communication is established between one opening of the plurality of openings and the lumen, the other openings of the plurality of openings and the lumen are not in fluid communication.

In another example, the medical device may further comprise an intermediary barrier, wherein the intermediary barrier is positioned between the barrier and the lumen, and wherein the intermediary barrier includes an intermediary opening positioned to be aligned with one of the plurality of openings via rotation of the barrier. The intermediary barrier may be rotatable relative to the barrier. The lumen may be a flexible catheter capable of traversing a tortuous body lumen, and further comprising a source of the pressurized gas.

According to an example, a medical device may comprise a cartridge including a plurality of chambers, wherein each of the chambers stores a pre-filled amount of agent, a lumen for receiving a pressurized gas, a channel establishing fluid communication between a first end of the cartridge and the lumen for delivering agent from the cartridge to the lumen, and a plunger coupled to a second end of the cartridge so that the plunger is aligned with one chamber of the plurality of chambers, wherein the plunger advances longitudinally into the one chamber, thereby pushing the pre-filled amount of agent towards the channel, and wherein the cartridge is rotatable relative to the plunger to align the plunger with another of the plurality of chambers. The plunger may be coupled to the cartridge so that the plunger is spring-biased to a position outside of the one chamber and aligned with the one chamber. The medical device may further comprise a trigger including a lever coupled to a linkage via a first articulating joint and a linkage coupled to a plunger via a second articulating joint.

According to an example, a method of administering an agent via a medical device may comprise positioning the medical device, including an enclosure, a barrier, and a lumen, so that a distal end of the lumen is adjacent to a targeted site, wherein the barrier is positioned between the enclosure and the lumen, the enclosure containing agent, and the barrier including at least one opening for storing the agent, providing a pressurized gas to the lumen, and rotating the barrier relative to the lumen so that fluid communication is established between the at least one opening and the lumen to deliver the agent from the at least one opening to the lumen. The method may further comprise rotating the barrier relative to the lumen so that the at least one opening and the lumen are not in fluid communication after a dose of the agent is delivered from the at least one opening to the lumen.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term “distal” refers to a portion farthest away from a user when introducing a device into a subject (e.g., patient). By contrast, the term “proximal” refers to a portion closest to the user when placing the device into the subject.

Both the foregoing general description and the following detailed description are exemplary and explanatory only and are not restrictive of the features, as claimed. As used herein, the terms “comprises,” “comprising,” “having,” “including,” or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, “about,” “substantially,” “generally,” and “approximately” are used to indicate a possible variation of ±10% in a stated value or characteristic.

The present disclosure may solve one or more of the limitations in the art. The scope of the disclosure, however, is defined by the attached claims and not the ability to solve a specific problem. The present disclosure is drawn to medical devices configured to administer doses of agents, e.g., therapeutic agents, among other aspects. The agent may be in any suitable form, including a powder form, which may be delivered to a stream of propellant/pressurized gas, e.g., $CO_2$, nitrogen, air, etc. Said medical devices allow for the administration of agents in metered doses, which allows for a greater consistency in the quantity of the agent that reaches a target site.

Figure 1A:
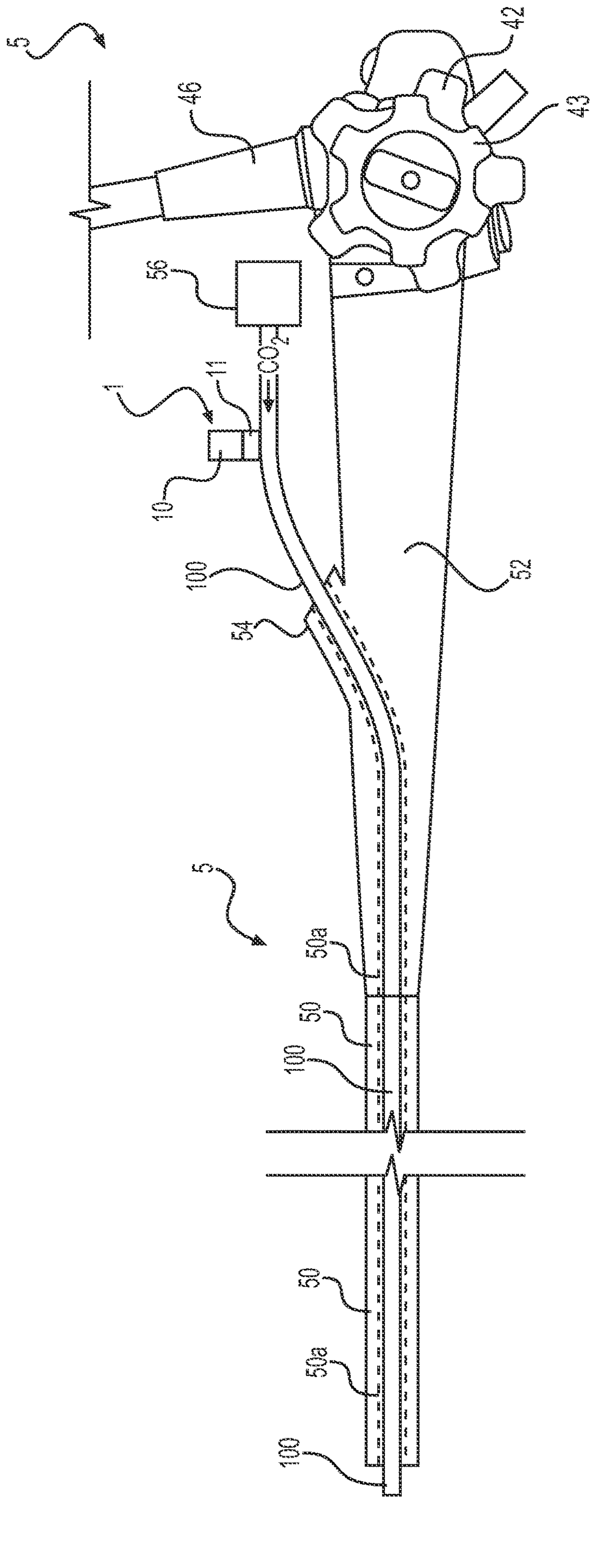
FIG. 1A is a side view of a portion of a shaft of an endoscope including a medical device, according to an embodiment.

Referring to FIG. 1A, a medical system 5, e.g., an endoscope, according to an embodiment is shown. Medical system 5 includes a flexible shaft 50 (e.g., a catheter) and a handle 52 connected at a proximal end of flexible shaft 50. Handle 52, or some other device for actuating or controlling medical system 5 and any tool or devices associated with medical system 5, includes first and second actuating devices 42, 43, which control articulation of flexible shaft 50, and/or an articulation joint at a distal end of flexible shaft 50, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of medical system 5 and connect to flexible shaft 50 to control movement thereof. Alternatively, or additionally, a user may operate actuating elements independently of handle 52. Distal ends of actuating elements may extend through flexible shaft 50 and terminate at an actuating joint and/or a distal tip of flexible shaft 50. For example, one or more actuating elements may be connected to an articulation joint, and actuation of actuating elements may control the actuating joint or the distal end of flexible shaft 50 to move in multiple directions.

In addition, one or more electrical cables (not shown) may extend from the proximal end of endoscope 5 to the distal end of flexible shaft 50 and may provide electrical controls to imaging, lighting, and/or other electrical devices at the distal end of flexible shaft 50, and may carry imaging signals from the distal end of flexible shaft 50 proximally to be processed and/or displayed on a display. Handle 52 may also include ports 54, 46 for introducing and/or removing tools, fluids, or other materials from the patient. Port 54 may be used to introduce tools. Port 46 may be connected to an umbilicus for introducing fluid, suction, and/or wiring for electronic components. For example, as shown in FIG. 1A, port 54 receives a tube 100, which extends from the proximal end to the distal end of flexible shaft 50, via a working channel 50*a* of shaft 50.

As shown in FIG. 1A, tube 100 of medical device 1 is attached to a pressurized gas source 56, e.g., $CO_2$, which may be controlled by a user to turn on/off and to adjust a rate at which gas flows into tube 100. Source 56 may be a gas canister or tank, a source of gas supplied by a medical facility, or any other suitable source. Medical device 1 further includes an enclosure 10, and a barrier 11 positioned between enclosure 10 and tube 100. Enclosure 10 and barrier 11 are coupled to a proximal portion of tube 100, distal of the connection between tube 100 and source 56.

Figure 1B:
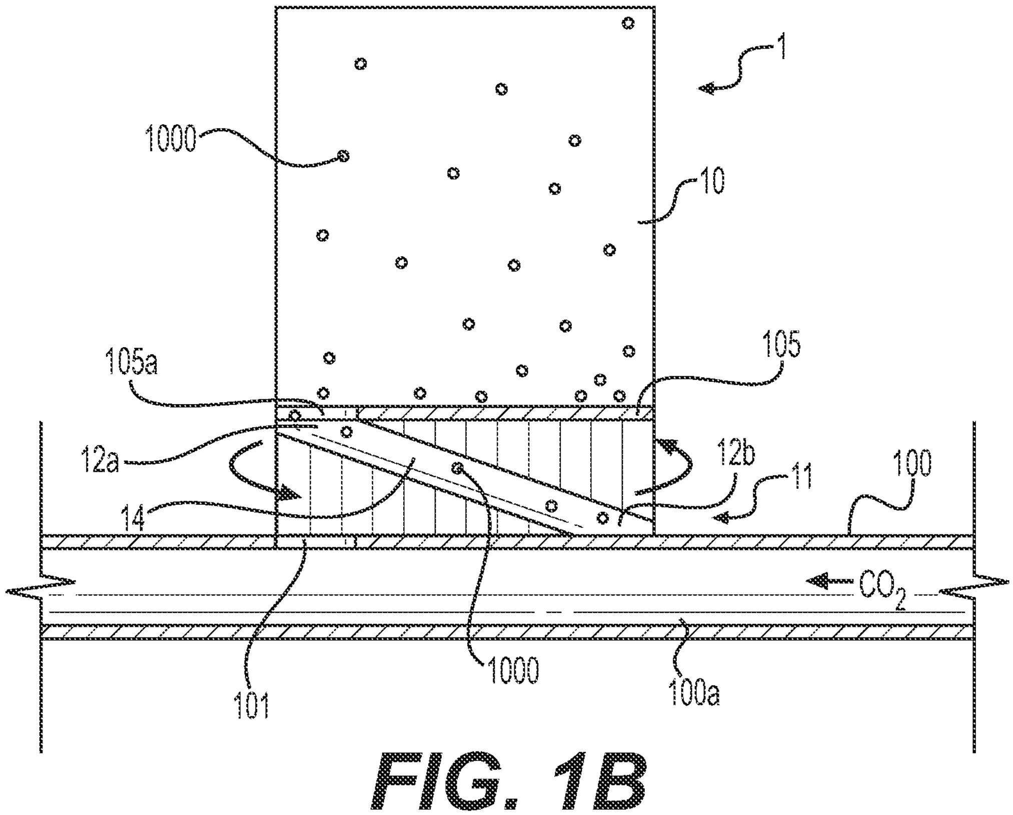
FIGS. 1B-C are cross-sectional views of the medical device of FIG. 1A.
Figure 1C:
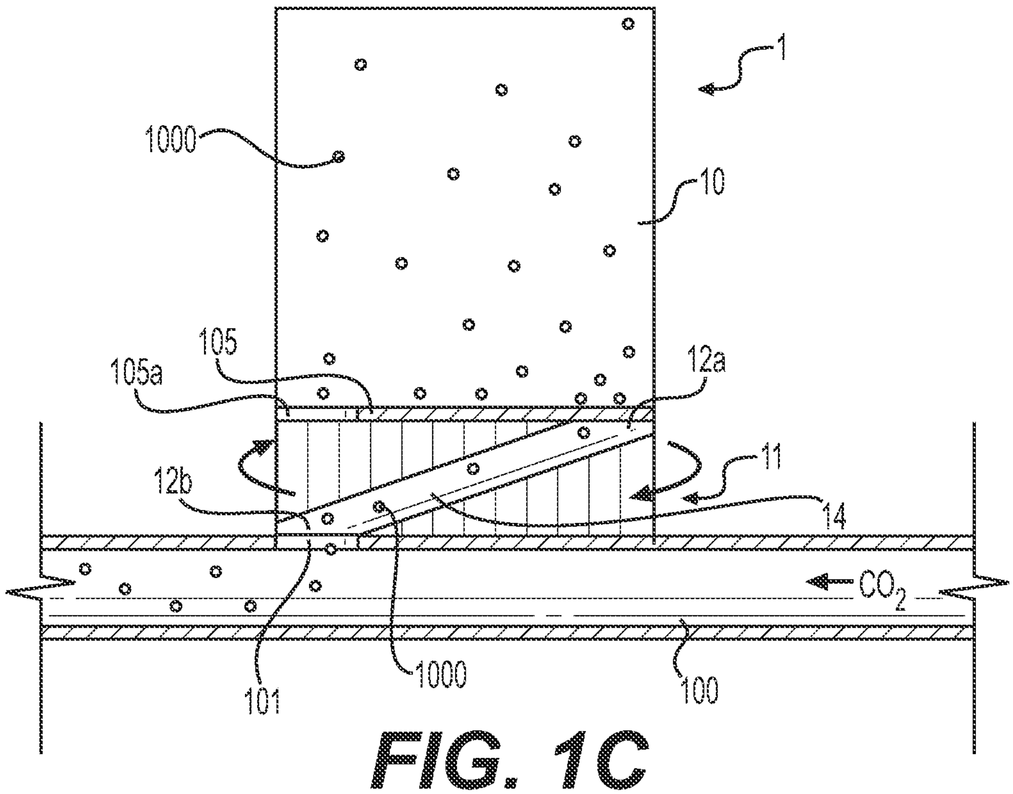

FIGS. 1B and 1C illustrate an embodiment of medical device 1, 1' in FIG. 1A in further detail. As discussed above, medical device 1 includes enclosure 10 defining a cavity for containing an agent 1000, a tube (e.g., a catheter or a sheath) 100 defining a lumen 100*a* receiving pressurized gas, e.g., $CO_2$, from a proximal end, and barrier 11 positioned between the cavity of enclosure 10 and lumen 100*a*. The shape or size of enclosure 10 is not particularly limited, and may be any suitable shape or size, including cylindrical. As indicated by the directional arrows in FIG. 1B, barrier 11 is rotatable relative to tube 100 and lumen 100*a*, e.g., about a central axis of barrier 11. In other embodiments, barrier 11 may be rotatable relative to both tube 100 and enclosure 10. In some other embodiments, enclosure 10 may be rotatable relative to barrier 11 and/or tube 100. Rotation of barrier 11 may be by any suitable action, for example, by hand or by mechanical, electrical, or pneumatic action.

Barrier 11 may be an annular, disk-like structure with openings and a passage therethrough. For example, barrier 11 includes a first opening 12*a* on the barrier surface (e.g., an upper surface) adjacent to the cavity of enclosure 10, for receiving agent 1000 in a passage 14 that extends through barrier 11. Barrier 11 further includes a second opening 12*b* on the opposite barrier surface (e.g., a bottom surface) adjacent to tube 100 and lumen 100*a*, from which agent 1000 may be dispensed into lumen 100*a*. It is noted that the size and shape of first opening 12*a* and second opening 12*b* are not particularly limited, and may be any suitable size or shape. First opening 12*a* and second opening 12*b* are located on opposite ends of barrier 11, but are connected via passage 14 extending across the length and thickness of barrier 11. Tube 100 also includes an opening 101 which may or may not be aligned with second opening 12*b* of barrier 11, depending on the rotational position of barrier 11 relative to tube 100 and lumen 100*a*. Thus, the rotation of barrier 11 relative to tube 100 may establish fluid communication between opening 12*b* and lumen 100*a* for delivering agent 1000 from passage 14 to lumen 100*a*. Enclosure 10 feeds opening 12*a* with agent 1000 via gravity, and passage 14 storing agent 1000 feeds lumen 100*a* with agent 1000 via gravity when second opening 12*b* and lumen opening 101 are aligned. In other embodiments, agent 1000 may be delivered to opening 12*a* and/or lumen 100*a* via other suitable mechanisms. Barrier 11 may also be rotated so that second opening 12*b* and opening 101 of lumen 100*a* are not aligned, thereby inhibiting the delivery of agent 1000 from passage 14 to lumen 100*a*. In this instance, passage 14 receives and stores agent 10000, until fluid communication between opening 12*b* of passage 14 and lumen 100*a* is established. It is noted that enclosure 10, in any rotational position of barrier 11, is not in fluid communication with lumen 100*a*. Furthermore, in embodiments prior to any use, passage 14 may be empty an without agent 1000.

In some embodiments, a bottom end of the cavity of enclosure 10 may include a wall 105 adjacent to barrier 11. Wall 105 may include an opening 105*a* that may or may not be aligned with opening 12*a* of barrier 11, depending on the rotational position of barrier 11 relative to enclosure 10. Thus, in such embodiments, barrier 11 and/or enclosure 10 may be rotated to align opening 105*a* with opening 12*a* of barrier 11 to deliver agent 1000 from enclosure 10 to passage 14 through opening 12*a*. This is illustrated in FIG. 1B, in which opening 105*a* of wall 105 and opening 12*a* of barrier 11 are aligned, thereby feeding passage 14 with agent 1000 from enclosure 10. FIG. 1C shows barrier 11 rotated by approximately 180° from its position in FIG. 1B relative to enclosure 10, and as a result, opening 105*a* of wall 105 and opening 12*a* are not aligned, being on opposite ends from one another. It is understood that the barrier 11 may be rotatable to any degree for alignment with opening 12*a*. Thus, opening 12*a* is sealed by wall 105, and agent 1000 is no longer fed into opening 12*a*. It is noted that opening 105*a* aligns with opening 12*a* when second opening 12*b* does not align with opening 101 of tube 100, and opening 105*a* does not align with opening 12*a* when second opening 12*b* aligns with opening 101 of tube 100. Thus, passage 14 may receive agent 1000, prior to agent 1000 being fed to lumen 100*a*. This allows for medical device 1 to administer a metered dose, i.e., the amount of agent 1000 stored in passage 14, per each degree of rotation, e.g., 180°, of barrier 11 and/or enclosure 10. Furthermore, in some other embodiments, both wall 105 and tube 100 may respectively include a plurality of openings. It is noted that passage 14 is capable of connecting openings of wall 105 and of tube 100 that are 180° apart. However, this is not desired, and in such embodiments, none of the openings of wall 105 are 180° apart from any of the openings of tube 100. As a result, there cannot be fluid communication between passage 14 and said openings of wall 105 and tube 100, at the same time. Instead, fluid communication between passage 14 and the openings of wall 105 and tube 100 is staggered, but not simultaneous. Such embodiments would allow for continuous rotation (both clockwise and counterclockwise) of barrier 11 relative to enclosure 10 to result in passage 14 receiving agent 1000 after a degree of rotation and subsequently dispensing agent 1000 after a further degree of rotation of barrier 11.

Referring to FIGS. 1A-1C, an example of how medical device 1 may be used is further discussed below. A user may deliver a distal end of tube 100 of medical device 1 into the body of a subject, e.g., via a natural orifice (such as a mouth or anus) and through a tortuous natural body lumen of the subject, such as an esophagus, stomach, colon, etc. Tube 100 may be delivered in any suitable way, for example, through working channel 50*a* of endoscope 5, by inserting a distal end of tube 100 into port 54 of endoscope 5. A user may direct/position the distal end of tube 100 to an intended target site for administration of agent 1000. A user may then fill enclosure 10 with agent 1000, if not filled already, and rotate barrier 11 and/or enclosure 10 relative to tube 100 and lumen 100*a* so that opening 105*a* aligns with opening 12*a*, thereby feeding passage 14 with agent 1000. As discussed above, when opening 105*a* aligns with opening 12*a*, second opening 12*b* does not align with opening 101 of tube 100. Thus, agent 1000 is received and stored by passage 14. A user may then rotate barrier 11 to align opening 12*b* with opening 101 of tube 100, so that all of agent 1000 stored in passage 14 is fed from passage 14 to lumen 100*a*, thereby administering a metered dose of agent 1000. A user may turn on the pressurized gas source at any time prior to the alignment of opening 12*b* with opening 101 and supply pressurized gas until the metered dose of agent 1000 reaches the target tissue site. Alternatively, a user may start supply of pressurized gas after the supply of agent 1000 to lumen 100*a*.

Figure 2A:
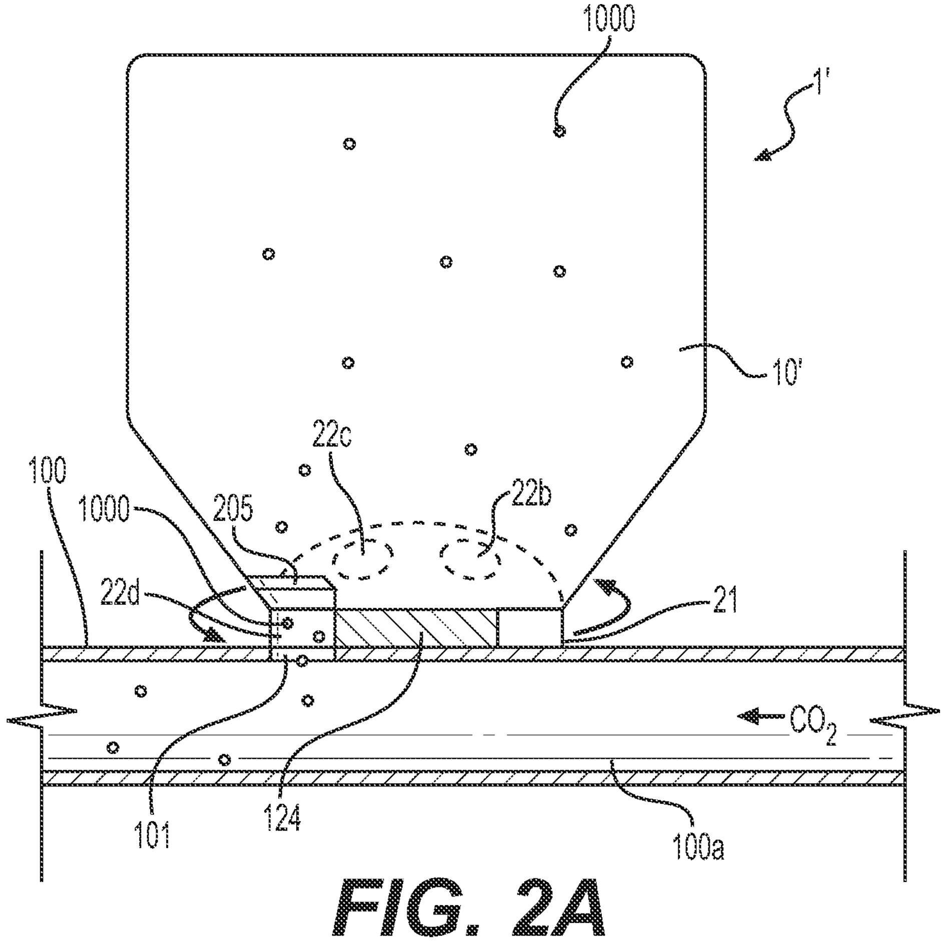
FIG. 2A is a cross-sectional view of a medical device, according to another embodiment.

In FIG. 2A, another embodiment of medical device 1' is shown. Like the embodiment discussed above, medical device 1' includes an enclosure 10' defining a cavity for containing an agent 1000, a tube (e.g., a catheter or a sheath) 100 defining a lumen 100*a* receiving pressurized gas, e.g., $CO_2$, from a proximal end, and a barrier 21 positioned between the cavity of enclosure 10 and lumen 100*a*. The shape or size of enclosure 10' is also not particularly limited, and may be any suitable shape or size. As indicated by the directional arrows in FIG. 2A, barrier 21 is also rotatable relative to tube 100 and lumen 100*a*. In other embodiments, barrier 21 may be rotatable relative to both tube 100 and enclosure 10'. In some other embodiments, enclosure 10' may be rotatable relative to barrier 21 and/or tube 100. Rotation of barrier 21 and enclosure 10' may also be actuated by any suitable action.

Figure 2B:
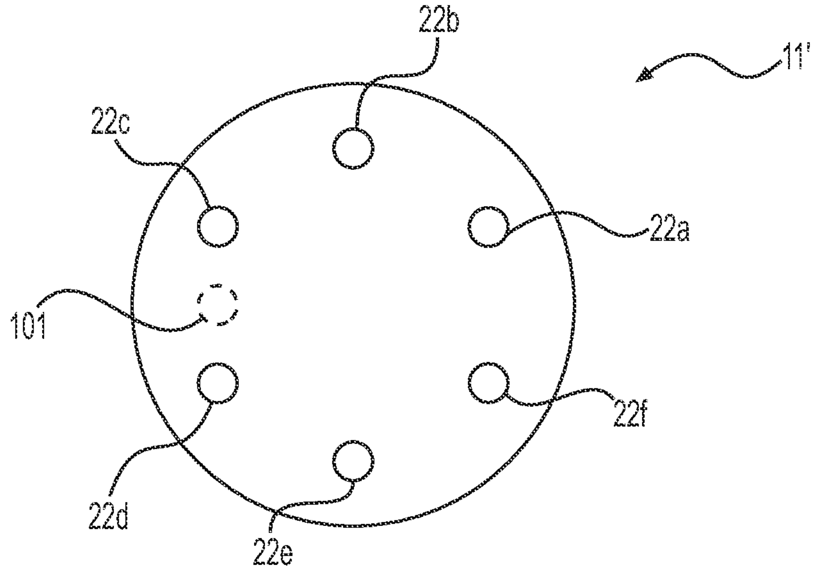
FIG. 2B is a top view of the barrier of FIG. 2A.

Barrier 21, as shown in both FIGS. 2A and 2B, includes a plurality of openings, i.e., six openings 22*a*-22*f*, of equal or approximately equal size, i.e., width or diameter, symmetrically arranged radially about a central axis of rotation of barrier 21. It is noted that the number of openings, the size of openings, the shape of openings, and the arrangement of openings on barrier 21 is not particularly limited, and may be any suitable configuration. For example, in other embodiments, barrier 21 may have four circular openings, each of which has varying diameters from one another. Each of openings 22*a*-22*f* extends through the thickness of barrier 21, and is configured to receive and store a pre-determined or selected amount of agent 1000, depending on the size of the openings. Thus, agent 1000 from enclosure 10 feeds into openings 22*a*-22*f*, via gravity in some embodiments, until said openings are filled. Note that FIG. 2A shows half of barrier 21 in perspective to show the position of openings 21*a*, 21*b*, 21*c*, and 21*d*.

By rotation of barrier 21 relative to tube 100 and lumen 100*a*, one of openings 22*a*-22*f* may align with opening 101, thereby establishing fluid communication between the one opening and lumen 100*a* for delivering agent 1000 from the one opening to lumen 100*a* via gravity. In some embodiments, enclosure 10' may further include a seal 205, which is positioned adjacently above barrier 21, above where one of openings 22*a*-22*f* may be located, and directly above opening 101 of tube 100. Thus, as one opening of openings 22*a*-22*f* aligns with opening 101 via rotation of barrier 21, an excess amount of agent 1000 above the one opening is shaved off by seal 205 and the one opening is sealed from receiving further agent 1000 from enclosure 10' when that opening aligns with opening 101 of tube 100. This allows for medical device 1' to administer a metered dose, i.e., the amount of agent 1000 stored in openings 22*a*-22*f*, per each degree of rotation, e.g., 60°, of barrier 21 and/or enclosure 10'. It is noted that as a result of such configuration, when fluid communication is established between one of openings 22*a*-22*f* and lumen 100*a*, no fluid communication is established between the other remaining openings and lumen 100*a*, as the bottom of the remaining openings is sealed by tube 100.

As shown in FIG. 2B, which shows a top view of barrier 21, barrier 21 may also be rotated so that none of openings 22*a*-22*f* are aligned with opening 101 of tube 100, thereby inhibiting the delivery of agent 1000 from any of openings 22*a*-22*f* to lumen 100*a*. In this instance, an amount of agent 1000 is stored in openings 22*a*-22*f* until fluid communication between the openings and lumen 100*a* is established.

Referring to FIGS. 2A-2B, an example of how medical device 1' may be used is further discussed below. Similar to medical device 1, medical device 1' may be delivered into the body of a subject, and directed to an intended target site for agent 1000 administration in the same manner. A user may then fill enclosure 10' with agent 1000, if not filled already, which will fill openings 22*a*-22*f* with agent 1000. The user then may rotate barrier 21 relative to tube 100 and lumen 100*a* so that one of openings 22*a*-22*f* aligns with opening 101. Such alignment results in seal 205 shaving off an excess amount of agent 1000 above the one opening, sealing the one opening from being fed any more of agent 1000 from enclosure 10', and feeding lumen 100*a* with agent 1000 stored in the one opening. As discussed above, when the one opening aligns with opening 101 of tube 100, the remaining openings 22*a*-22*f* do not align with opening 101 of tube 100. Thus, agent 1000 is stored within the remaining openings 22*a*-22*f*, until each of the remaining openings is aligned with opening 101 via rotation of barrier 21, in turn. A user may turn on the pressurized gas source at any time prior to or during the alignment of one of the openings 22*a*-22*f* with opening 101, as in the embodiment described in connection with FIGS. 1B-1C.

Figure 3A:
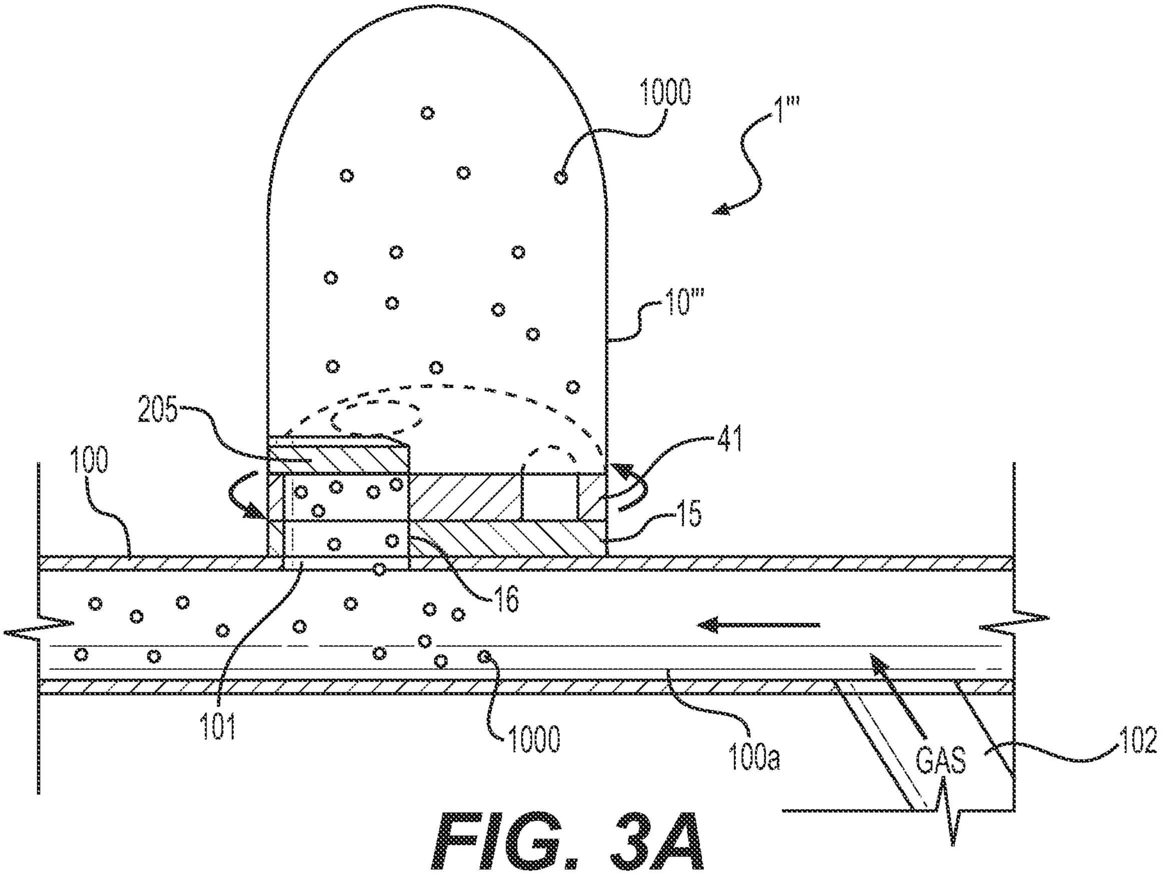
FIG. 3A is a cross-sectional view of a medical device, according to another embodiment.

In FIG. 3A, another embodiment of medical device 1''' is shown. Medical device 1''' is similar to medical device 1', and differences between the two devices will be highlighted. Device 1''' may include any of the features of device 1' and operate in the same or substantially the same way. Medical device 1''' includes an enclosure 10''', a barrier 41, and lumen 100. Moreover, enclosure 10''' further includes a seal 205, which is positioned adjacently above barrier 41, above where one of openings 42*a*-42*c* may be located, and directly above opening 101 of tube 100. However, unlike medical device 1', lumen 100*a* of medical device 1''' receives pressurized gas from a second lumen 102, which is connected to tube 100 at a point that is proximal to opening 101. Alternatively, medical device 1''' may receive pressurized gas from a proximal end of lumen 100*a*, and may be without second lumen 102. Medical device 1''' further includes, in at least some embodiments, an intermediary barrier 15 including an opening 16, positioned between barrier 41 and tube 100. As indicated by the directional arrows in FIG. 3A, barrier 41 is rotatable relative to intermediary barrier 15, tube 100, and lumen 100*a*. In other embodiments, enclosure 10''' may also be rotatable relative to barrier 41, intermediary barrier 15, tube 100, and lumen 100*a*. Rotation of enclosure 10''' and barrier 41 may be actuated by any suitable action.

Figure 3B:
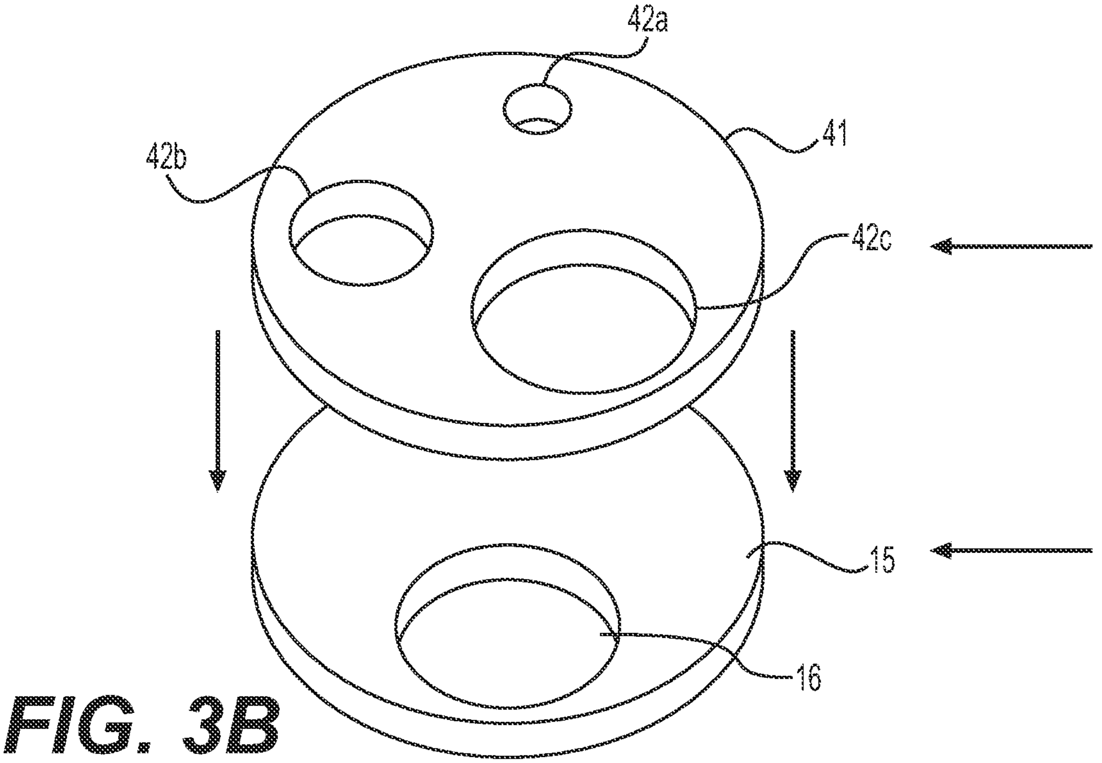
FIG. 3B is a top perspective view of the barrier of FIG. 3A over the intermediary barrier of FIG. 3A.

Barrier 41, as shown in both FIGS. 3A and 3B, includes three openings, i.e., 42*a*-42*c*, of different sizes, i.e., widths or diameter, arranged radially about a central axis of rotation of barrier 41, like barrier 21 (referring to FIG. 2B). A first opening 42*a* has the smallest width of the three openings, a second opening 42*c* has the largest width of the three openings, and a third opening 42*b* has a width in between that of first opening 42*a* and that of second opening 42*c*. Thus, each of openings 42*a*-42*c* receives and stores different amounts or doses of agent 1000.

To help a user differentiate between the different sizes of openings 42*a*-42*c*, enclosure 10''' and/or barrier 41 may further include markings on their outer surfaces that indicate the locations of openings 42*a*-42*c* relative to one another, and to openings 16 and 101. Thus, a user may rotate barrier 41 and/or enclosure 10'', relative to intermediary barrier 15, tube 100, and lumen 100*a*, to select one of openings 42*a*-42*c* based on a desired amount or dose of agent 1000.

Intermediary barrier 15, as shown in both FIGS. 3A and 3B, includes opening 16. Opening 16 may be aligned with lumen opening 101, and also openings 42*a*-42*c*, depending on the rotational position of barrier 41 relative to intermediary barrier 15. As shown in FIG. 3B, opening 16 is at least the same width as the largest opening of barrier 41, i.e., second opening 42*c*.

Any one of openings 42*a*-42*c* may be aligned with intermediary opening 16 and lumen opening 101 via rotation of barrier 21. Such alignment establishes fluid communication between one of openings 42*a*-42*c* and lumen 100*a* for delivering agent 1000 from one of openings 42*a*-42*c* to lumen 100*a* via gravity. Similar to that of medical device 1', as one opening of openings 42*a*-42*c* aligns with opening 16 of intermediary barrier 15 and opening 101 via rotation of barrier 41, an excess amount of agent 1000 above the one opening is shaved off by seal 205 and the one opening is sealed from further receiving agent 1000 from enclosure 10'''. This allows for medical device 1''' to administer a metered dose, the amount of agent 1000 stored in openings 42*a*-42*c*, per each degree of rotation, e.g., 120°, of barrier 41. As a result of such configuration, when fluid communication is established between one of openings 42*a*-42*c* and lumen 100*a*, no fluid communication is established between the other remaining openings 42*a*-42*c* and lumen 100*a*.

Barrier 41 may also be rotated so that none of openings 42*a*-42*c* is aligned with intermediary opening 16 and lumen opening 101, thereby inhibiting the delivery of agent 1000 from enclosure 10''' to lumen 100*a*. In this instance, varying amounts of agent 1000 are stored in openings 42*a*-42*c* until fluid communication between openings 42*a*-42*c* and lumen 100*a* is established.

It is further noted in some embodiments, intermediary barrier 15 may also be rotatable relative to enclosure 10''', barrier 41, tube 100, and lumen 100*a*, so that opening 16 does not align with any of the openings of barrier 41, and/or opening 101 as well. This is applicable in embodiments having barriers with multiple openings. By being able to misalign opening 16 from opening 101, a user may select another opening 42*a*, 42*b*, 42*c*, etc., via rotation of barrier 41, that is not adjacent to the currently aligned opening, without having to inadvertently dispense agent 1000 stored in openings adjacent to the currently aligned opening, via the necessary degree of rotation to select other non-adjacent openings.

Referring to FIGS. 3A-3B, an example of how medical device 1''' may be used is further discussed below. Similar to medical devices 1 and 1', medical device 1''' may be delivered into the body of a subject, and directed to an intended target site for agent 1000 administration in the same manner. A user may then fill enclosure 10' with agent 1000, if not filled already, and rotate barrier 41 relative to intermediary barrier 15, tube 100, and lumen 100*a*, so that one of openings 42*a*-42*c* aligns with openings 16 and 101. Such alignment results in seal 205 shaving off an excess amount of agent 1000 above the one opening, sealing the one opening from being fed any more of agent 1000 from enclosure 10'', and feeding lumen 100*a* with agent 1000 stored in the one opening. As discussed above, when the one opening aligns with opening 16 of intermediary barrier 15 and opening 101 of tube 100, the remaining openings 42*a*-42*c* do not align with openings 16 and 101. Thus, agent 1000 is stored within the remaining openings 42*a*-42*c*, until each of the remaining openings is aligned with openings 16 and 101 via rotation of barrier 41. A user may turn on the pressurized gas source at any time prior to or during the alignment of one of the openings 42*a*-42*c* with openings 16 and 101, as in previously described embodiments.

Figure 4A:
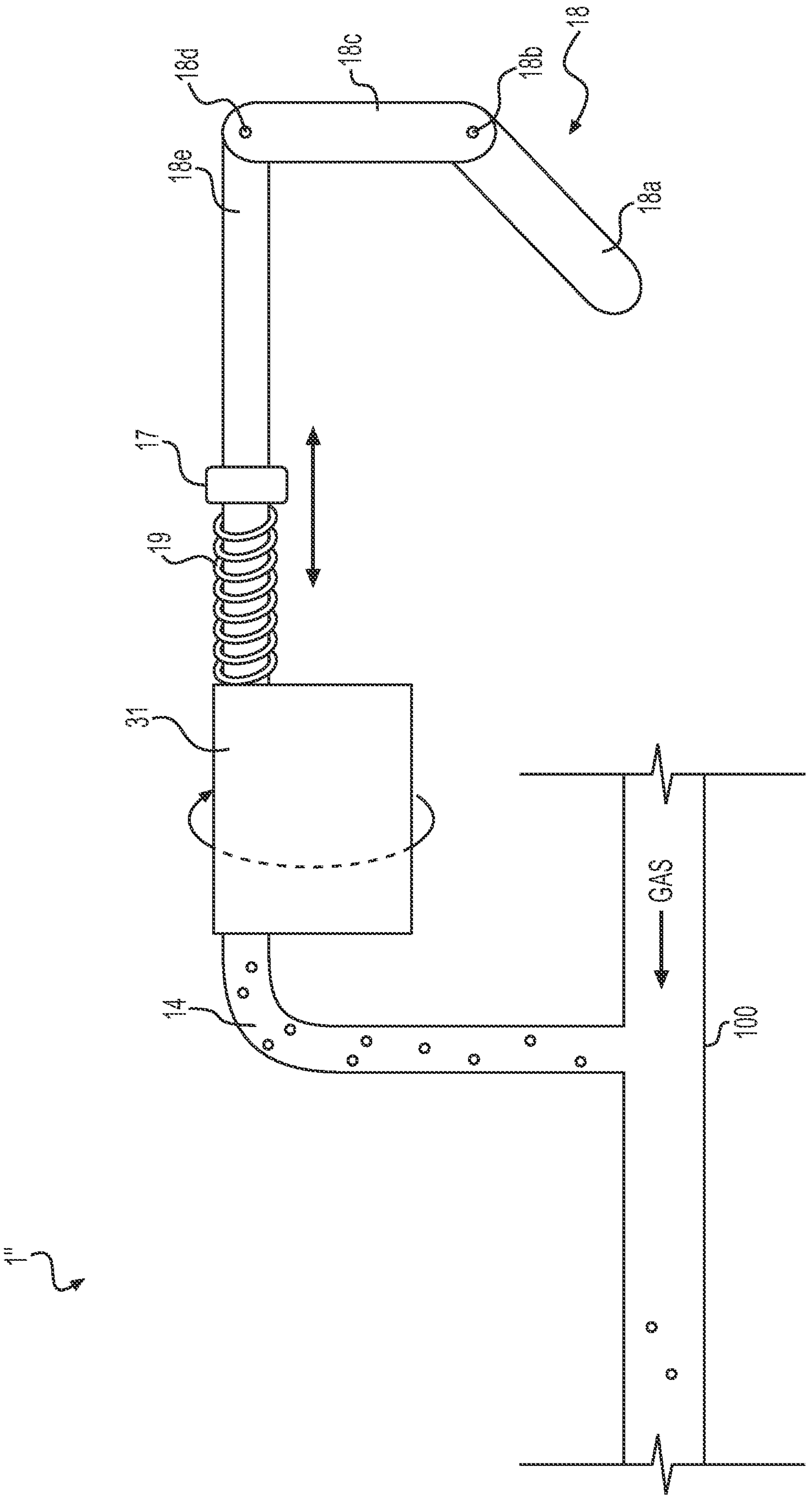
FIG. 4A is a side view of a medical device, according to another embodiment.
Figure 4B:
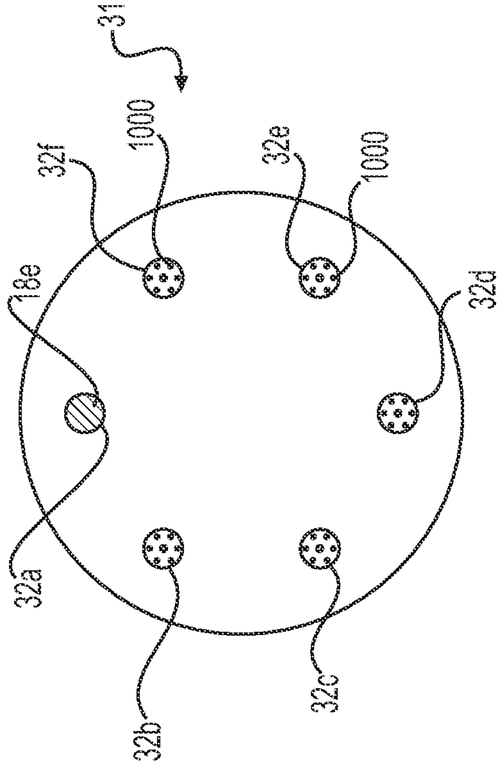
FIG. 4B is a top view of the cartridge of FIG. 4A.

Referring to FIG. 4A, another embodiment of medical device 1'' is shown. Medical device 1'' includes a trigger 18, a rotating cartridge 31 including a plurality of chambers, a lumen 100 receiving pressurized gas from a proximal end, and a channel 14 establishing fluid communication between a distal end of cartridge 31 and lumen 100 for delivering agent 1000 from cartridge 31 to lumen 100. As shown in FIG. 4B, cartridge 31 includes a plurality of symmetrically-arranged chambers, i.e., six chambers 32*a*-32*f*, of equal or substantially equal size, each of which stores a pre-filled amount of agent 1000.

Trigger 18 includes a lever 18*a* coupled to a linkage 18*c* via an articulating joint 18*b*, and linkage 18*c* coupled to a plunger 18*e* via another articulating joint 18*d*. A distal portion of plunger 18*e* is housed within a proximal portion of cartridge 31, and is coupled to cartridge 31 in any suitable manner so that the distal end of plunger 18*e* faces one of chambers 32*a*-32*f* with which plunger 18*e* is aligned. A spring 19 coils around a distal portion of plunger 18*e* outside of cartridge 31 up until a stop 17 fixated on plunger 18*e*, thereby spring-biasing plunger 18*e* in its aforementioned position of facing one of chambers 32*a*-32*f*. Spring 19 is not particularly limited and may be any suitable spring. Likewise, stop 17 may be of any suitable material, such as rubber.

Trigger 18 is configured so that when lever 18*a* is pulled proximally, linkage 18*c* likewise pivots proximally relative to plunger 18*e* via articulating joint 18*d*. Such movements of lever 18*a* and linkage 18*c* result in plunger 18*e* longitudinally advancing towards cartridge 31 and into one of chambers 32*a*-32*f*, thereby propelling the pre-filled amount of agent 1000 towards and through channel 14, which extends downward to tube 100, thereby feeding agent 1000 to tube 100 via gravity. The longitudinal advancement of plunger 18*e* may be actuated by any suitable mechanisms, including, but not limited to, mechanical, electrical, or pneumatic mechanisms. Plunger 18*e* advances within cartridge 31 and one of chambers 32*a*-32*f* up until spring 19 is fully compressed, thereby inhibiting any further advancement of plunger 18*e* towards cartridge 31. Once lever 18 is released, spring-biased plunger 18*e* automatically reverts back to its initial position of being outside of and facing one of chambers 32*a*-32*f*.

Cartridge 31 is rotatable relative to plunger 18*e* so that any one of chambers 32*a*-32*f* is aligned with plunger 18*e*. In some embodiments, cartridge 31 may be configured to rotate or revolve automatically, after one of chambers 32*a*-32*f* is emptied by plunger 18*e*, so that an adjacent chamber 32*a*-32*f* storing a pre-filled amount of agent 1000 is aligned with plunger 18*e*.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:

an enclosure defining a cavity for containing agent;

a lumen for receiving a pressurized gas; and a barrier positioned between the cavity and the lumen, the barrier including a passage extending through the barrier for storing agent received from the enclosure, wherein rotation of the barrier relative to the lumen establishes fluid communication between the passage and the lumen for delivering agent received from the enclosure to the lumen via the passage;

wherein the barrier includes a first opening and a second opening positioned on opposing ends of the barrier, the first opening is connected to the second opening via the passage.

2. The medical device according to claim 1, wherein a bottom end of the cavity includes a wall adjacent to the barrier, wherein the wall includes a wall opening, wherein the wall opening is located on an area of the wall so that the wall opening is aligned with the first opening via rotation of the barrier.

3. The medical device according to claim 2, wherein alignment of the wall opening with the first opening permits agent from the enclosure to enter the passage.

4. The medical device according to claim 1, wherein the enclosure is rotatable relative to the barrier and/or the lumen.

5. The medical device according to claim 1, wherein the barrier is rotatable relative to the enclosure.

6. The medical device according to claim 1, wherein the agent remains in the passage until fluid communication between the passage and the lumen is established.

7. The medical device according to claim 1, wherein the enclosure feeds the passage with agent via gravity.

8. The medical device according to claim 1, wherein the passage for storing agent feeds the lumen with agent via gravity when fluid communication between the passage and the lumen is established.

9. The medical device according to claim 1, wherein the lumen is a flexible catheter capable of traversing a tortuous body lumen, and further comprising a source of the pressurized gas.

10. A method of administering an agent via a medical device, comprising:

positioning the medical device, including an enclosure, a barrier, and a lumen, so that a distal end of the lumen is adjacent to a targeted site, wherein the barrier is positioned between the enclosure and the lumen, the enclosure containing the agent, and the barrier including a first opening and a second opening positioned on opposing ends of the barrier, and a passage extending through the barrier between the first opening and the second opening, the passage is configured for connecting the first opening to the second opening and storing the agent received from the enclosure;

providing a pressurized gas to the lumen; and rotating the barrier relative to the lumen so that fluid communication is established between the passage and the lumen to deliver the agent from the passage to the lumen.

11. The method according to claim 10, further comprising:

rotating the barrier relative to the lumen so that the passage and the lumen are not in fluid communication after a dose of the agent is delivered from the passage to the lumen.

12. The medical device according to claim 1, wherein the barrier is configured to seal the first opening, thereby inhibiting the passage from receiving the agent from the cavity.

13. The medical device according to claim 9, wherein the source of the pressurized gas is configured to supply the pressurized fluid, thereby moving the agent received from the passage through the lumen.

14. A medical device, comprising:

an enclosure storing an agent;

a lumen; and a barrier positioned between the enclosure and the lumen, the barrier including a first opening, a second opening positioned opposite of the first opening, and a passage extending through the barrier between the first opening and the second opening such that the first opening is in fluid communication with the second opening via the passage;

wherein the barrier is configured to rotate relative to the enclosure and the lumen for establishing fluid communication between the passage and each of the enclosure and the lumen;

wherein, in response to aligning the first opening with the enclosure, the barrier is configured to receive the agent from the enclosure and into the passage via the first opening, and in response to aligning the second opening with the lumen, the barrier is configured to deliver the agent received from the enclosure in the passage into the lumen via the second opening.

15. The medical device according to claim 14, wherein a bottom wall of the enclosure includes an opening, and the barrier is configured to align the first opening with the opening on the bottom wall of the enclosure in response to rotating the barrier relative to the enclosure and the lumen.

16. The medical device according to claim 14, wherein a top wall of the lumen includes an opening, and the barrier is configured to align the second opening with the opening on the top wall of the lumen in response to rotating the barrier relative to the enclosure and the lumen.

17. The medical device according to claim 14, wherein the enclosure feeds the passage with the agent via gravity, and the passage feeds the lumen with the agent via gravity.

18. The medical device according to claim 14, wherein the agent enters the passage when the first opening is in fluid communication with the enclosure and exits the passage when the second opening is in fluid communication with the lumen.

19. The medical device according to claim 14, wherein the barrier is configured to seal the first opening, thereby inhibiting the passage from receiving the agent from the enclosure; and wherein the barrier is configured to seal the second opening, thereby inhibiting the lumen from receiving the agent from the passage.

20. The medical device according to claim 14, furthering comprising a source of the pressurized gas that is configured to move the agent received from the passage through the lumen.

* * * * *